United States Patent [19]
Yoon

[11] Patent Number: 5,922,002
[45] Date of Patent: *Jul. 13, 1999

[54] SURGICAL INSTRUMENT WITH JAWS AND MOVABLE INTERNAL BIOPSY DEVICE AND METHOD FOR USE THEREOF

[76] Inventor: InBae Yoon, 2101 Highland Ridge Dr., Phoenix, Md. 21131

[*] Notice: This patent is subject to a terminal disclaimer.

[21] Appl. No.: 08/847,185

[22] Filed: May 1, 1997

Related U.S. Application Data

[63] Continuation-in-part of application No. 08/376,186, Jan. 20, 1995., Pat. No. 5,665,100, which is a continuation-in-part of application No. 08/281,814, Jul. 28, 1994., abandoned, which is a continuation of application No. 08/073,193, Jun. 8, 1993., Pat. No. 5,334,209, which is a continuation of application No. 07/720,381, Jun. 25, 1991., Pat. No. 5,217,473, which is a division of application No. 07/446,555, Dec. 5, 1989., Pat. No. 5,026,379

[51] Int. Cl.$^6$ ..................................................... A61B 17/32
[52] U.S. Cl. .......................... 606/170; 606/205; 606/139; 606/144
[58] Field of Search ..................................... 606/151, 205, 606/207, 170, 142, 144, 139, 148, 149, 167

[56] References Cited

U.S. PATENT DOCUMENTS

| | | |
|---|---|---|
| 2,002,594 | 3/1935 | Wappler et al. . |
| 2,004,559 | 11/1935 | Wappler et al. . |
| 2,028,635 | 9/1936 | Wappler . |
| 4,077,412 | 3/1978 | Moossun . |
| 4,103,680 | 8/1978 | Yoon . |
| 4,174,715 | 11/1979 | Hasson . |
| 4,249,533 | 2/1981 | Komiya . |
| 4,257,420 | 3/1981 | Terayama . |
| 4,372,295 | 2/1983 | Heckele . |
| 4,374,523 | 2/1983 | Yoon . |
| 4,393,872 | 7/1983 | Reznik et al. . |
| 4,427,014 | 1/1984 | Bel et al. . |
| 4,471,766 | 9/1984 | Terayama . |
| 4,557,255 | 12/1985 | Goodman . |
| 4,598,699 | 7/1986 | Garren et al. . |
| 4,788,966 | 12/1988 | Yoon . |
| 4,869,268 | 9/1989 | Yoon . |
| 4,966,583 | 10/1990 | Debbas . |
| 5,025,778 | 6/1991 | Silverstein et al. . |
| 5,037,433 | 8/1991 | Wilk et al. . |
| 5,139,487 | 8/1992 | Baber . |
| 5,147,373 | 9/1992 | Ferzli . |
| 5,176,695 | 1/1993 | Dulebohn . |
| 5,190,541 | 3/1993 | Abele et al. . |
| 5,211,650 | 5/1993 | Noda . |
| 5,217,460 | 6/1993 | Knoepfler . |
| 5,226,908 | 7/1993 | Yoon . |
| 5,234,443 | 8/1993 | Phan et al. . |
| 5,261,917 | 11/1993 | Hasson et al. . |
| 5,312,391 | 5/1994 | Wilk . |
| 5,318,589 | 6/1994 | Lichtman . |

(List continued on next page.)

*Primary Examiner*—Michael Buiz
*Assistant Examiner*—Daphna Shai
*Attorney, Agent, or Firm*—Blank Rome Comisky & McCauley LLP

[57] ABSTRACT

A surgical instrument includes a forceps unit for being positioned within an anatomical cavity and an inner member having a biopsy tool. The forceps unit includes a housing, an outer tubular member, an intermediate member, and a handle mechanism coupled with at least one of the intermediate and outer tubular members for creating relative movement between the intermediate and outer tubular members. The outer tubular member has a proximal end mounted on the housing and terminates distally at a distal end. The intermediate member has a tubular body disposed telescopically within the outer tubular member, a proximal end mounted in the housing and an integral one-piece distal end defining a pair of opposed jaws resiliently biased apart such that relative movement of the outer tubular member distal end over the jaws causes the jaws to close. The inner member includes a tubular member removably disposed at least partly within the intermediate member and carrying a biopsy tool that can be selectively advanced into the jaws.

21 Claims, 10 Drawing Sheets

U.S. PATENT DOCUMENTS

| | | |
|---|---|---|
| 5,324,254 | 6/1994 | Phillips . |
| 5,336,231 | 8/1994 | Adair . |
| 5,348,555 | 9/1994 | Zinnanti . |
| 5,366,476 | 11/1994 | Noda . |
| 5,398,670 | 3/1995 | Ortiz et al. . |
| 5,403,332 | 4/1995 | Christoudias . |
| 5,462,561 | 10/1995 | Voda . |
| 5,462,562 | 10/1995 | Elkus . |
| 5,476,505 | 12/1995 | Limon . |
| 5,496,310 | 3/1996 | Exconde et al. . |
| 5,538,008 | 7/1996 | Crowe . |
| 5,542,949 | 8/1996 | Yoon . |
| 5,549,623 | 8/1996 | Sharpe et al. . |
| 5,562,102 | 10/1996 | Taylor . |
| 5,569,241 | 10/1996 | Edwards . |
| 5,578,007 | 11/1996 | Imran . |
| 5,607,435 | 3/1997 | Sachdeva et al. . |
| 5,611,813 | 3/1997 | Lichtman . |
| 5,620,459 | 4/1997 | Lichtman . |
| 5,746,770 | 5/1998 | Zeitels et al. . |
| 5,766,169 | 6/1998 | Fritzsch et al. . |

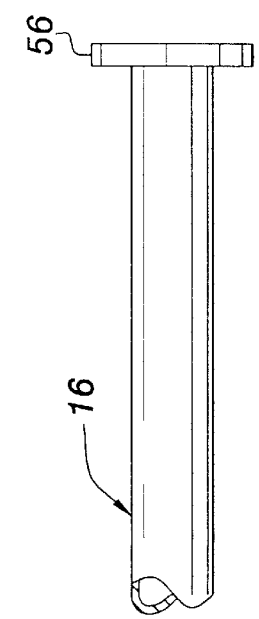
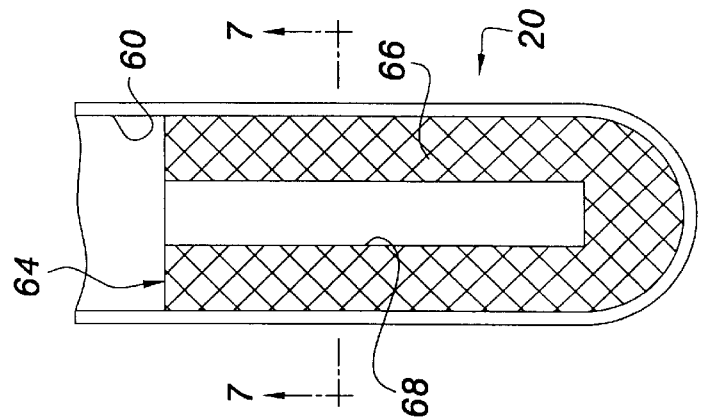
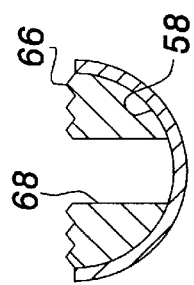
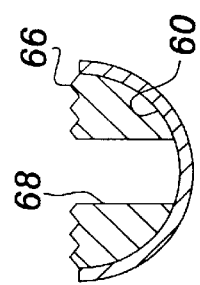
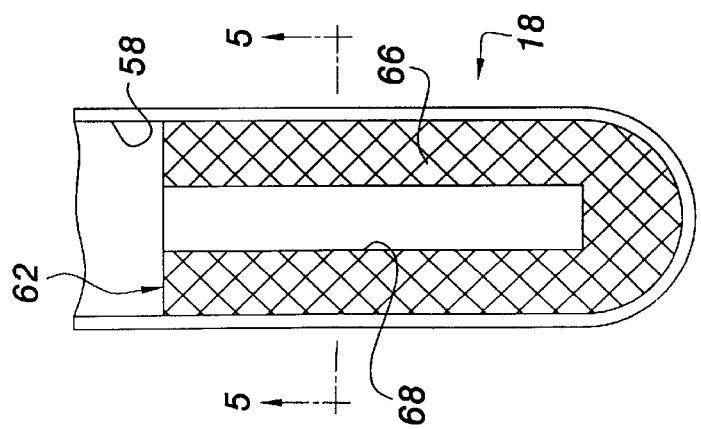

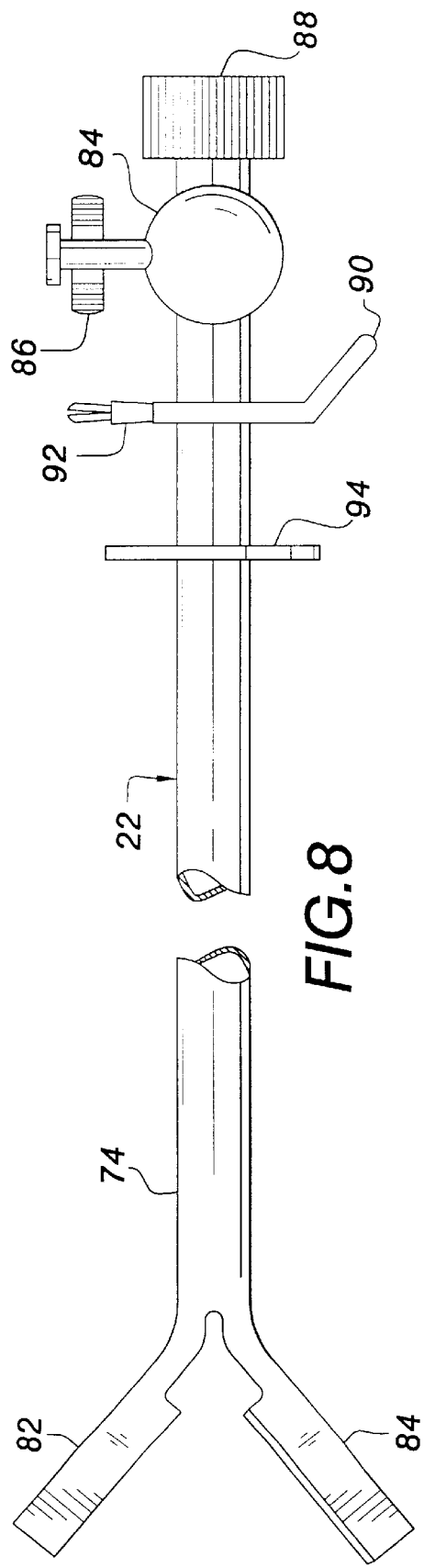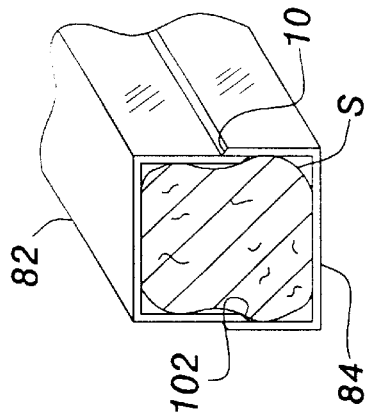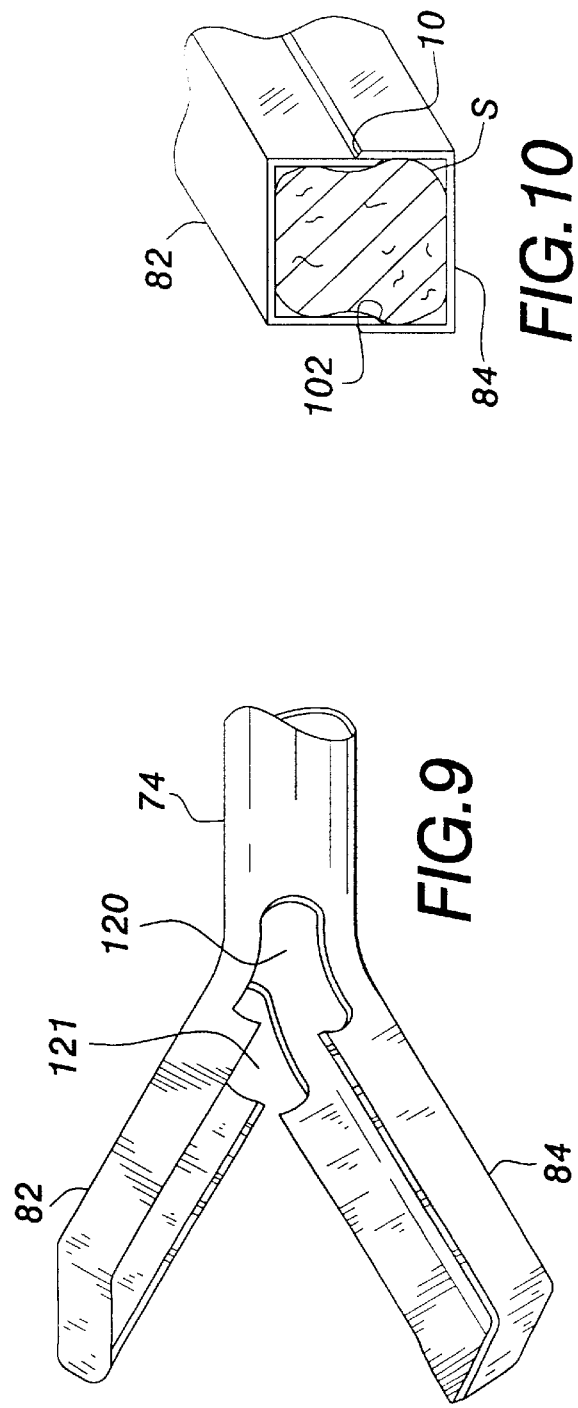

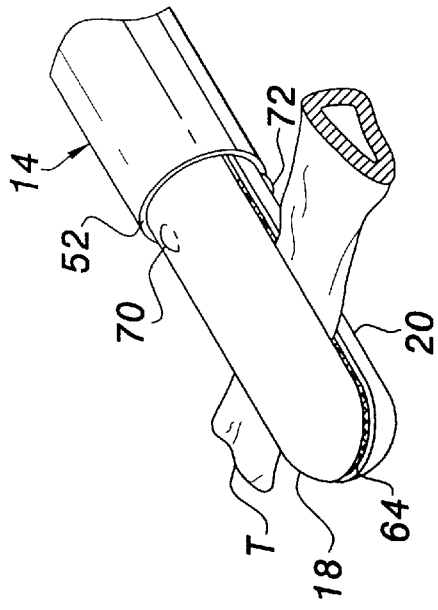
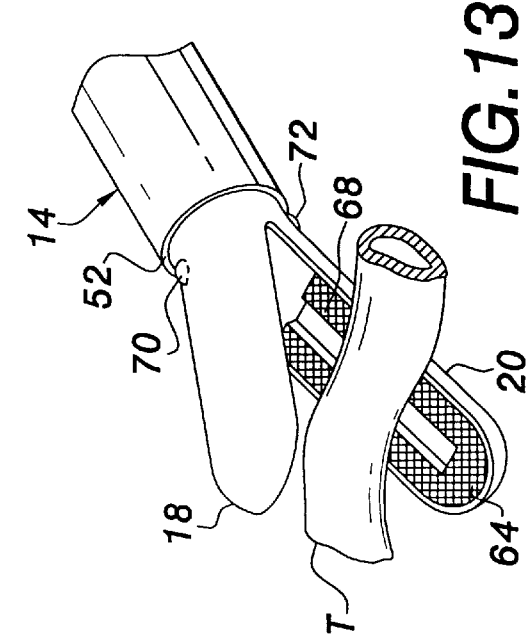
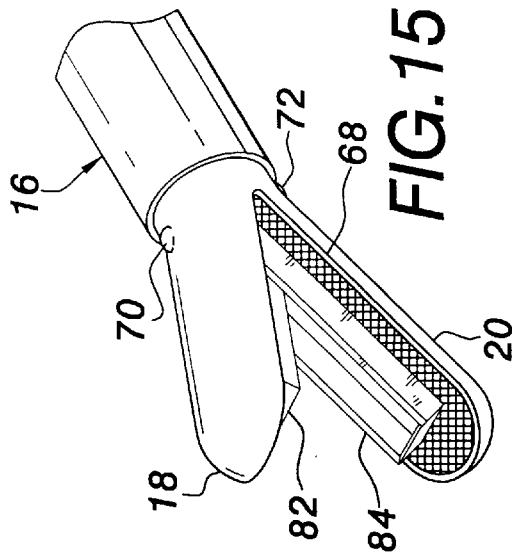

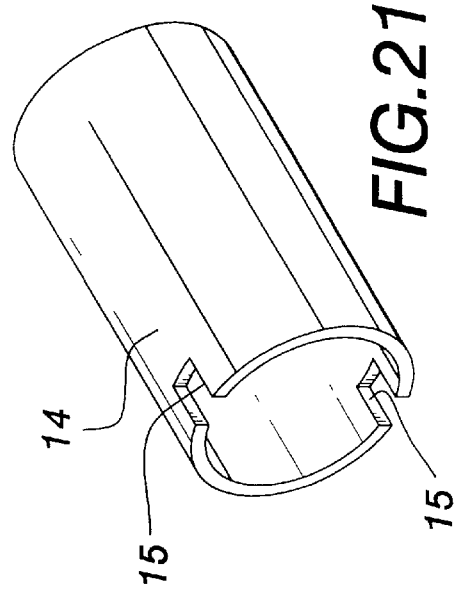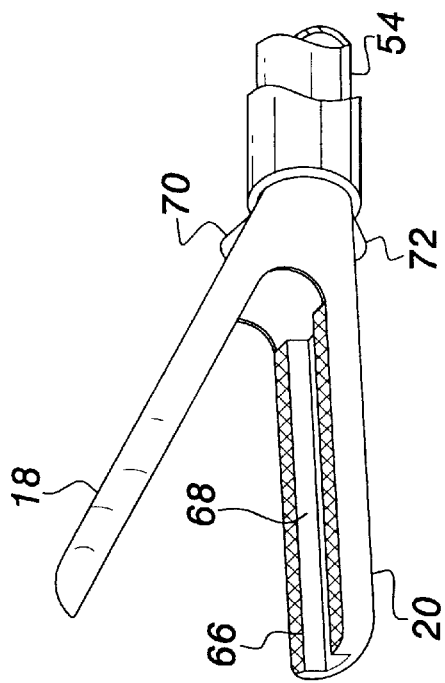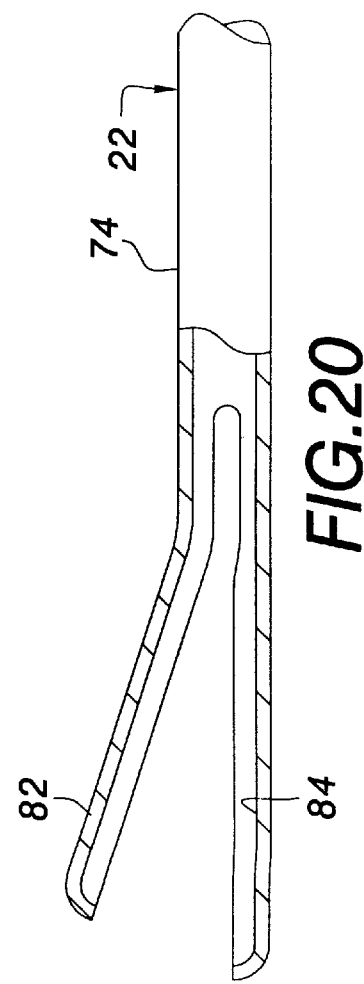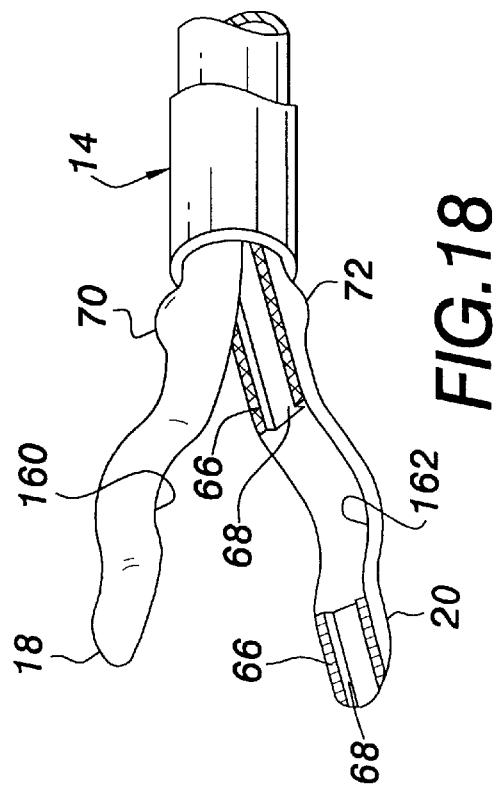

SURGICAL INSTRUMENT WITH JAWS AND MOVABLE INTERNAL BIOPSY DEVICE AND METHOD FOR USE THEREOF

CROSS-REFERENCE TO RELATED APPLICATIONS

This application is a continuation-in-part of Ser. No. 08/376,186, filed on Jan. 20, 1995, now U.S. Pat. No. 5,665,100, which is a continuation-in-part of applicant's application Ser. No. 08/281,814, filed Jul. 28, 1994, abandoned which is a continuation of patent application Ser. No. 08/073,193, filed Jun. 8, 1993, now U.S. Pat. No. 5,334,209, which is a continuation of patent application Ser. No. 07/720,381, filed Jun. 25, 1991, now U.S. Pat. No. 5,217,473, which is a divisional of patent application Ser. No. 07/446,555, filed Dec. 5, 1989, now U.S. Pat. No. 5,026,379, the disclosures of which are incorporated herein by reference.

BACKGROUND OF THE INVENTION

1. Field of the Invention

The present invention relates generally to medical procedures and instruments and, more particularly, to a multifunctional instrument having jaws, a central channel and a moveable inner member having a biopsy tool for performing endoscopic procedures.

2. Discussion of the Related Art

Endoscopic and minimally invasive medical procedures, such as laparoscopy, have become widely accepted for surgery and diagnosis due to the associated advantages relating to reduced trauma and hospitalization time. The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, ligating appliers, forceps, cauteries and the like into the anatomical cavity.

Endoscopic procedures commonly involve performing a number of individual acts or functions within the anatomical cavity including grasping, cutting, coagulating, irrigating, aspirating, puncturing, injecting, dissecting, cauterizing, ligating, suturing, illuminating, visualizing and/or collecting specimens for biopsy. However, typical endoscopic instruments are capable of performing at most two of the above functions, requiring several incisions for placement of multiple portal sleeves to accommodate a suitable number of endoscopic instruments for performing the required functions or necessitating frequent withdrawal and replacement of individual endoscopic instruments through a single incision. While it is generally desirable to minimize the number of incisions created for performing a particular endoscopic procedure, substitution of instruments through a single incision can be time consuming, depending on the efficiency of the medical facility and staff, increasing the period of anesthetization for the patient. Additionally, internal bleeding can develop during the substitution of instruments thereby obscuring the field of view and requiring time consuming cleanup procedures to be performed.

A disadvantage of endoscopic instruments having articulated jaws, in particular, is that the jaws are typically mounted on pivots at the distal end of relatively long shafts requiring complicated and space-consuming linkages for converting the user's proximal movements into motion of the jaws and increasing the risk of fluid leaking through poorly sealed pivotal mounts.

Also, it is often desirable to grasp and manipulate tissue prior to or subsequent to obtaining a biopsy sample. Conventional devices do not facilitate this procedure through a single incision without changing instruments.

SUMMARY OF THE INVENTION

Accordingly, it is a primary object of the present invention to overcome the above mentioned disadvantages of the prior art with an endoscopic instrument capable of performing multiple functions, such as grasping and biopsy sample collection.

Another object of the present invention is to minimize the number of incisions required for performing an endoscopic procedure by performing multiple functions through a single incision with an endoscopic instrument having a forceps unit with jaws for performing grasping and manipulating functions and a movable biopsy tool in a central channel formed through the jaws for collecting biopsy samples.

It is another object of the present invention to lock jaws of an endoscopic instrument together to ensure smooth entry of the endoscopic instrument through a portal sleeve and to prevent inadvertent snagging of anatomical tissue.

An additional object of the invention is to selectively grasp tissue and collect biopsy samples using the same mechanism.

Some of the advantages of the present invention over the prior art are that the endoscopic instrument can perform multiple functions through a single incision thereby minimizing the number of incisions required to perform an endoscopic procedure, that use of an endoscopic instrument for picking-up and holding objects is simplified, that objects can be held without the need for exerting continuous hand or finger pressure, that single-handed operation of a forceps unit and a biopsy tool is facilitated, that conventional handle structures can be used to provide surgeons with a familiar feel and to decrease adaptation time, that the instrument can be fabricated at low cost using simple mechanisms without complicated linkages, and that the instrument can be sterilized for reuse or disposable for single patient use as desired.

The present invention is generally characterized in an endoscopic instrument including a forceps unit for being positioned within an anatomical cavity and a moveable inner member disposed in a central channel formed through the forceps unit. The forceps unit includes a housing, an outer tubular member, an intermediate member, and a handle mechanism coupled with at least one of the intermediate and outer tubular members for creating relative movement therebetween. The outer tubular member has a proximal end mounted on the housing and terminates distally at a distal end. The intermediate member has a tubular body disposed telescopically within the outer tubular member, a proximal end mounted in the housing and an integral one-piece distal end defining a pair of opposed jaws resiliently biased apart such that relative movement of the outer tubular member distal end over the jaws causes the jaws to close. The movable inner member includes a tubular member slidably disposed at least partly within the intermediate member and having a biopsy tool on a distal end thereof for collecting tissue for biopsy.

A further aspect of the present invention is generally characterized in a method of performing an endoscopic procedure including the steps of introducing a tubular member with integral one-piece jaws through an opening in an anatomical cavity wall, manipulating anatomical tissue with the jaws, opening the jaws, advancing a moveable inner member having a biopsy tool distally through a central channel in the tubular member to place the biopsy device between the jaws, and collecting a biopsy sample with the inner member.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 3 illustrates the intermediate member of the preferred embodiment removed from the outer member for illustrative purposes;

FIG. 4 illustrates one jaw of the preferred embodiment;

FIG. 5 illustrates the jaw of FIG. 4 in section taken along line 5—5;

FIG. 6 illustrates the other jaw of the preferred embodiment;

FIG. 7 illustrates the jaw of FIG. 6 in section taken along line 7—7;

FIG. 8 illustrates the inner member of the preferred embodiment removed form the intermediate member and the outer member for illustrative purposes;

FIG. 9 is a perspective view of the distal end of the inner member;

FIG. 10 is a sectional view of the biopsy boxes with a tissue sample therein;

FIG. 13 illustrates the jaws of the preferred embodiment before grasping tissue;

FIG. 14 illustrates the jaws of the preferred embodiment grasping tissue;

FIG. 15 illustrates the jaws of the preferred embodiment in an open position with the inner member advanced;

FIG. 18 illustrates a modification to the jaws of the preferred embodiment;

FIG. 19 illustrates another modification to the jaws of the preferred embodiment;

FIG. 20 illustrates a modification to the distal end of the inner member that is suitable for use with the modified jaws of FIG. 19; and FIG. 21 illustrates a modification of the outer member.

DETAILED DESCRIPTION OF THE PREFERRED EMBODIMENT

The endoscopic instrument of the present invention can be utilized in any type of anatomical cavity; and, accordingly, while the instrument is described hereinafter for use with a portal sleeve in endoscopic procedures, such as laparoscopy, the instrument can be used with catheters and other small and large diameter cylindrical members providing access to small cavities, such as veins and arteries, as well as large cavities, such as the abdomen.

Figure 1:
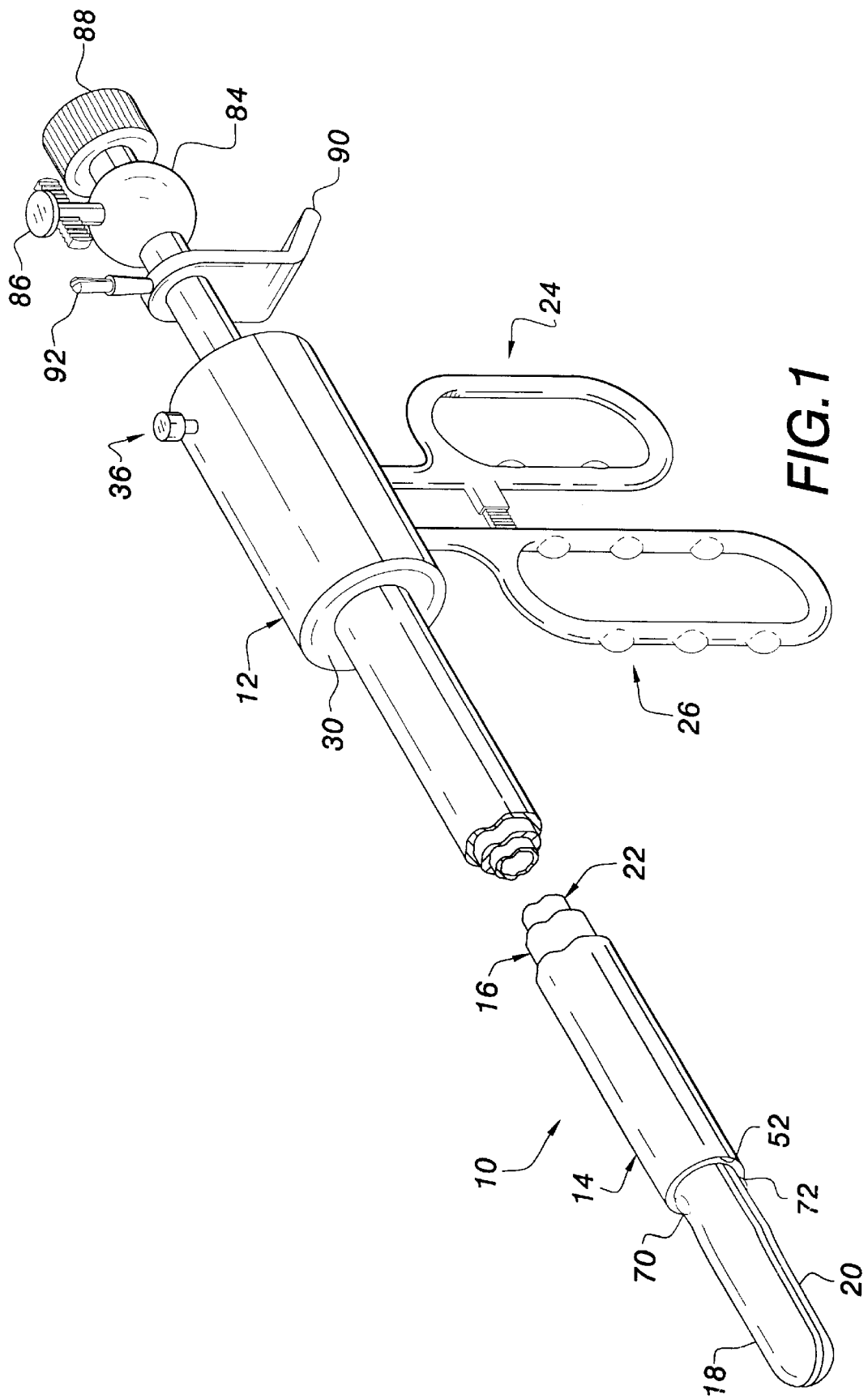
FIG. 1 is a perspective view, broken longitudinally, of an endoscopic instrument according to the present invention.

Endoscopic instrument 10 according to a preferred embodiment of the present invention, as shown in FIG. 1, includes housing 12, tubular outer member 14 extending distally from housing 12, tubular intermediate member 16 telescopically fitted within outer tubular member 14 and having opposed jaws 18 and 20 on a distal end thereof, fixed handle 24 and movable handle 26 extending from the housing at an angle relative to the longitudinal axis of instrument 10, and inner member 22 which is at least partly telescopically fitted within intermediate tubular member 16.

Figure 2:
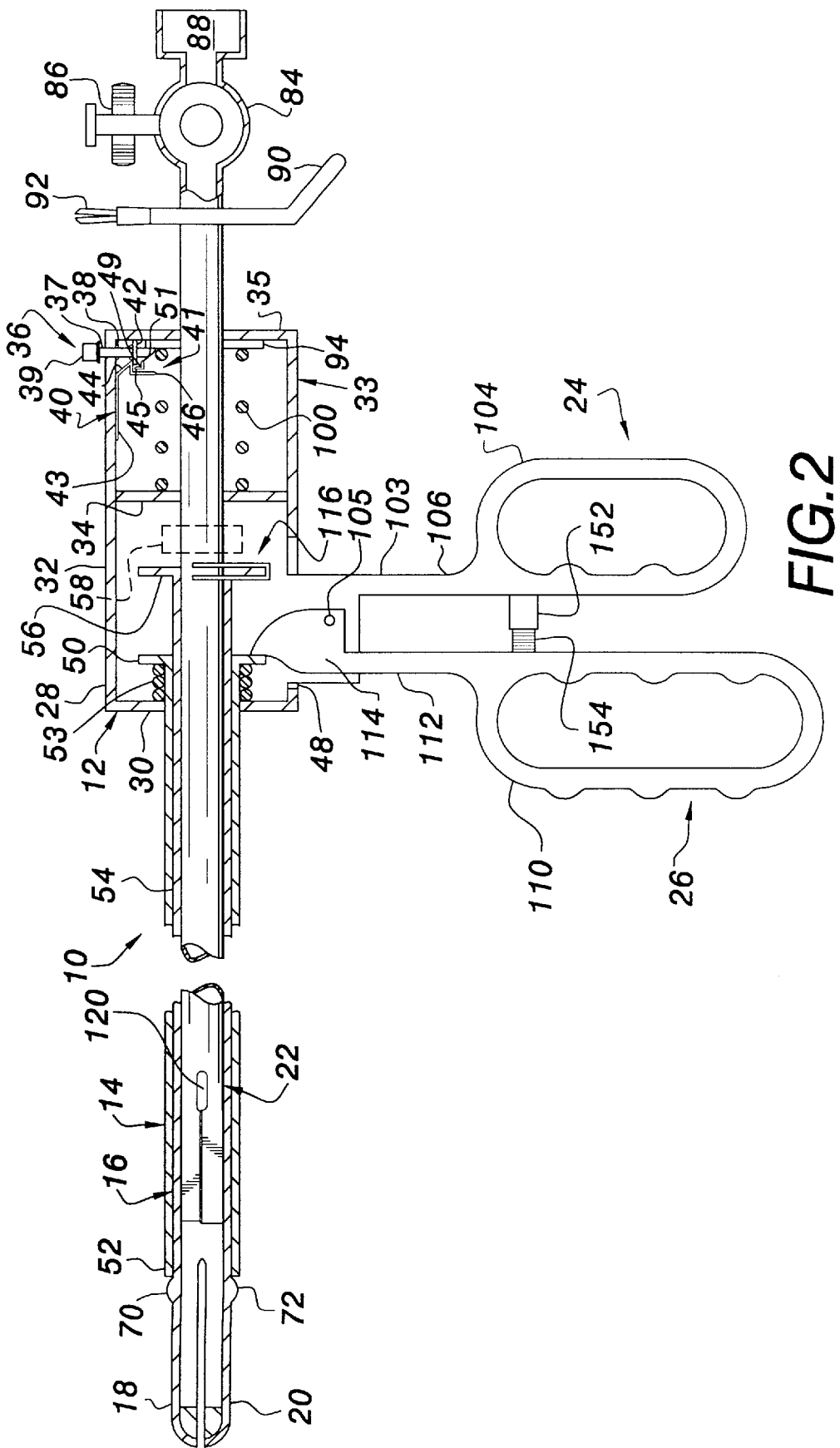
FIG. 2 illustrates the preferred embodiment in section.

As shown in FIG. 2, housing 12 is generally tubular with cylindrical sidewall 28 and front and rear walls 30 and 31 closing opposite ends of cylindrical sidewall 28. Intermediate wall 34 divides housing 12 into two compartments. Slotted opening 48 is formed in cylindrical sidewall 28 of housing 12 and extends longitudinally between front wall 30 and intermediate wall 34 of housing 12 to permit movable handle 26 to pass therethrough. Fixed handle 24 extends from plate 103 formed on housing 12 proximate slot 48. Plate 103 can be formed integrally with housing 12 or can be fixedly attached to housing 12 to be stationary relative thereto.

Outer member 14 is open at both ends and extends through an opening in front wall 30 to terminate proximally at transverse flange 50 disposed between front wall 30 and intermediate wall 34. Distal end 52 of outer tubular member 14 can be blunt as shown, tapered, beveled or chamfered as desired or have any other suitable distal configuration. Preferably, outer member 14 is made of a substantially cylindrical length of a substantially rigid material, such as stainless steel or other medically acceptable plastic or metal material.

Intermediate member 16 includes tubular body 54 telescopically fitted within outer tubular member 14. Tubular body 54 terminates proximally at transverse flange 56 disposed within housing 12 between flange 50 and housing rear wall 34; and, as best seen in FIG. 3 which shows intermediate member 16 removed from outer member 14 for illustrative purposes, a distal end of tubular body 54 is split longitudinally to form integral one-piece jaws 18 and 20 that oppose one another. Jaws 18 and 20 are normally biased apart as shown and define opposed semicylindrical recesses 58 and 60 (see FIGS. 5 and 7) for carrying jaw inserts 62 and 64. Jaw inserts 62 and 64 can be permanently or removably secured within semicylindrical recesses 58 and 60 respectively using adhesives, detents, or any other suitable method of attachment or can be formed with jaws 18 and 20 as an integral one-piece construction.

Each of inserts 62 and 64 defines grasping surface or tread 66 suitable for grasping anatomical tissue or holding instruments such as a needle and longitudinal slot or groove 68 extending from a proximal end of insert 62 and 64 to a position proximally spaced from the distal end of insert 62 and 64. A repeated pattern of diamond-shaped protrusions is shown for tread 66. However, other surfaces such as those having parallel ribs or textured portions could be used. The length, width and depth of each groove 68 will depend on the size of any biopsy tool carried by inner member 22 as will be described in more detail below. Wedge-like cams 70 and 72 are formed on respective exterior surfaces of jaws 18 and 20 and are distally spaced from outer member distal end 52 when jaws 18 and 20 are fully open. Cams 70 and 72 taper toward the joint region or junction where each of jaws 18 and 20 connects with the tubular body 54.

As best seen in FIG. 3, tubular body 54 of intermediate member 16 is preferably formed with jaws 18 and 20 as a single unitary part using a resilient medically-acceptable material such as a spring steel or plastic having suitable elastic properties for normally biasing the upper and lower jaws 18 and 20 apart while permitting jaws 18 and 20 to be moved towards one another in response to axial forces acting on jaws 18 and 20 as a result of relative movement between outer tubular member 14 and intermediate member 16. Referring again to FIG. 2, it can be seen that bias member 53 is connected between flange 50 and front wall 30 such that outer member 14 is normally biased in a proximal direction relative to intermediate member 16. Bias member 53 is shown as a helical coil spring disposed around intermediate member 16 and held in compression between flange 50 and front wall 30. However, bias member 53 can be constituted of various other types of springs as well as other types of bias devices including tension springs, torsion springs, pan springs, leaf springs, rubber, plastic or magnets, for example.

As best seen in FIGS. 8 and 9 which illustrate inner member 22 removed from outer member 14 and intermediate member 16 for illustrative purposes, inner member 22 includes a cylindrical or tubular shaft 74 and a biopsy tool in the form of a pair of opposed biopsy box members 82 and 84. Biopsy box members 82 and 84 are preferably formed integrally with tubular shaft 74 as a unitary piece and are resiliently biased apart to fit within grooves 68 of jaws 18 and 20 when inner member is advanced distally as described below. Box members 82 and 84 can have any configuration in cross-section, for example semi-cylindrical or rectangular, for defining opposed cavities 86 and 88 and cooperating to form a tissue-receiving container when closed as shown in FIG. 10. Respective peripheral edges of cavities 86 and 88 are configured to form opposed cutting surfaces 101 and 102 for cutting samples S from anatomical tissue between jaws 18 and 20 when jaws 18 and 20 are closed thereby pressing box members 82 and 84 together. Cutting surfaces 101 and 102 can be arranged relative to one another as shown in FIG. 10 for sliding contact to perform a scissor-like cut or for direct abutment to perform a chopping cut when box members 82 and 84 are pressed together by jaws 18 and 20. When tissue sample S is collected within biopsy box members 82 and 84, inner member 22 can be retracted into intermediate member 16 in the manner disclosed below to protect sample S during withdrawal from the anatomical cavity or to allow further manipulation of tissue with jaws 18 and 20.

Referring to FIG. 2, tubular shaft 74 of inner member 22 is telescopically fitted within the tubular portion of intermediate member 16 and extends through aligned openings in front wall 30, rear wall 31 and intermediate wall 34 of housing 12 to terminate proximally outside housing 12 at spherical reservoir 85 with proximal aperture 88 and a stop cock valve 86 disposed within reservoir 85 for controlling passage of instruments and/or fluids through aperture 88 and into tubular shaft 74.

Handle 90 extends transversely from tubular shaft 74 near the proximal end of tubular shaft 74 and is angled proximally to form a finger rest. Insulated connector 92 can be provided to permit electrical conductors to enter tubular shaft 74 on a side opposite handle 90 to be connected with electrically conductive elements of the instrument for performing unipolar or bipolar electric coagulation, for example using jaws 18 and 20 or biopsy box members 82 and 84 as a conductive element. Tubular shaft 74 also carries transverse flange 94 disposed within housing 12 between rear wall 31 and intermediate wall 34 (see FIG. 2). Bias member 100, shown as a helical coil spring, is disposed around tubular shaft 74 and held in compression between flange 94 and intermediate wall 34 to bias inner member 22 proximally within housing 12 and intermediate member 16.

Inner member 22 is prevented from being inadvertently moved in a distal direction by a safety mechanism 36 disposed within housing 12 as shown in FIG. 2 and disclosed in detail in the parent application. A push-button type of safety mechanism 36 is shown whereby inner tubular member 22 can be locked in a retracted position with flange 94 abutting rear wall 31 by depressing button 39 and can subsequently be released prior to being moved distally by depressing button 39 a second time. It will be appreciated, however, that other safety mechanisms can be used, including rotatable levers, detents, and splined collars for example. Safety mechanism 36 includes post 37 extending radially through housing 12, bias member 38 connected between post 37 and housing 12 for biasing post 37 radially outward, push-button 39 mounted on top of post 37 externally of housing 12 latch spring 40 disposed within housing 12 for engaging post 37 in a locked position where a lower end of post 37 engages flange 94, and trigger 41 for releasing latch spring 40 to allow post 37 to move radially outward to an unlocked position. Post 37 is oriented transversely relative to the longitudinal axis of inner member 22 and includes annular flange 42 disposed within housing 12. Bias member 38 is shown as a helical coil spring disposed around post 37 and held in tension between housing 12 and annular flange 42 to bias post 37 radially outward of housing 12. Latch spring 40 is formed of a resilient strip of material configured to have flat base 43 secured to an outer wall of the hub and downwardly angled arm 44 extending from a proximal end of base 43 toward the post 37. Arm 44 bends back on itself to form latching surface 45 that is substantially parallel annular flange 42. Transverse extension 46 of arm 44 extends from a distal end of latching surface 45 in parallel to post 37. Trigger 41 is disposed proximate arm extension 46 and is pivotally mounted in housing 12. Trigger 41 is generally L-shaped and has leg 49 overlying arm extension 46 and leg 51 extending transversely from leg 49 and at a slight downward angle, to be disposed beneath annular flange 42 when post 37 is in the locked position shown in FIG. 2. A torsion spring (not shown) can be connected between trigger 41 and housing 12 to bias trigger 41 in a counterclockwise direction in FIG. 2 such that leg 49 is normally in contact with the arm extension 46.

Referring still to FIG. 2, it will be seen that movable handle 26 is pivotally mounted on pin 105 secured to plate 103. Fixed handle 24 includes finger loop 104 configured to accommodate one or more fingers of the surgeon and shank 106 connecting finger loop 104 with mounting plate 103. Movable handle 26 includes finger loop 110 configured to accommodate one or more fingers of the surgeon and shank 112 connecting finger loop 110 with flattened end portion 114 which extends through slotted opening 48 into housing 12 towards flange 50 of outer member 14. Intermediate member 16 is fixed to housing 12 by bracket 116. Therefore, when movable handle 26 is pressed towards fixed handle 24, flattened portion 114 presses flange 50 distally. This pushes outer member 14 at least partly over cams 70 and 72 to close jaws 18 and 20.

A pair of mating protrusions 152 and 154 are carried at opposed locations on finger loops 104 and 110 respectively to lock handles 24 and 26 together when pressed towards one another a predetermined angular distance corresponding to a desired resultant position of jaws 18 and 20. Mating protrusions 152 and 154 are shown having serrated inside surfaces, but can have any other configuration to ratchet, mate frictionally and/or latch together when engaged.

Use of endoscopic instrument 10 of the present invention is illustrated in FIGS. 11–16, wherein instrument 10 is shown being guided through portal sleeve 156 positioned in wall W of an anatomical cavity. Instrument 10 is preferably passed through portal sleeve 156 with jaws 18 and 20 at least partly closed so that instrument 10 can be inserted without catching on anatomical tissue or snagging structure within portal sleeve 156. Since outer member 14 can be held by protrusions 152 and 154 in a position partly closing the jaws, the surgeon need not exert any force on handles 14 and 26 of instrument 10 during insertion.

Figure 11:
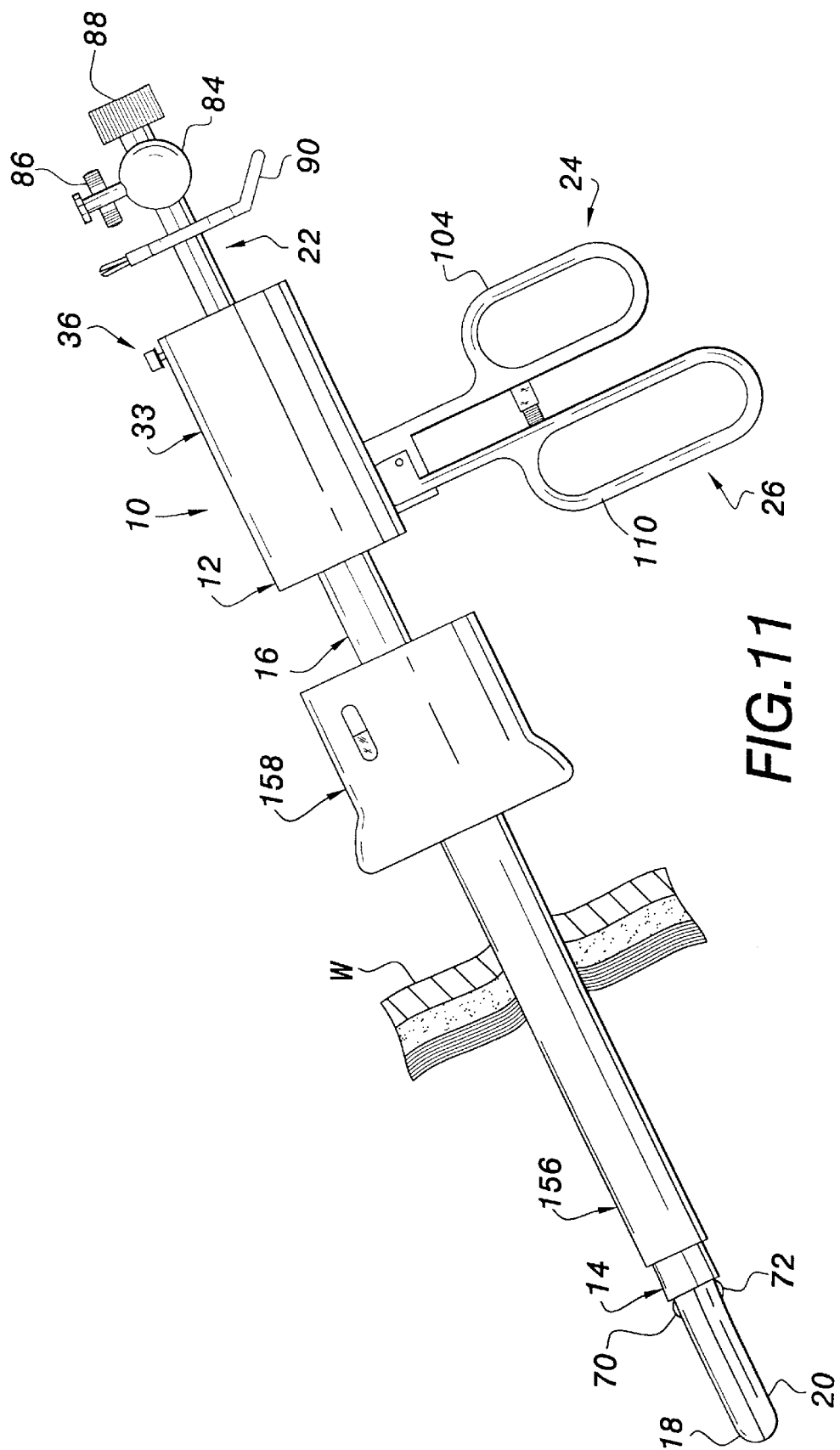
FIG. 11 illustrates the preferred embodiment in use.

With jaws 18 and 20 at least partly closed, endoscopic instrument 10 is inserted through portal sleeve 156 positioned within the anatomical cavity wall W, as shown in FIG. 11, to access an operative site within the anatomical cavity. Portal sleeve 156 can be positioned in wall W using any suitable penetrating technique, including those creating puncture sites by means of removable obturators such as trocars, and is shown carrying valve housing 158 at a proximal end to prevent the loss of pneumoperitoneum during insertion and withdrawal of endoscopic instrument 10. Visualization of the endoscopic procedure can be accomplished using a conventional endoscope (not shown) incorporated into endoscopic instrument 10, for example within tubular shaft 74, or separately positioned within the anatomical cavity through a second portal sleeve located at another puncture site.

Figure 12:
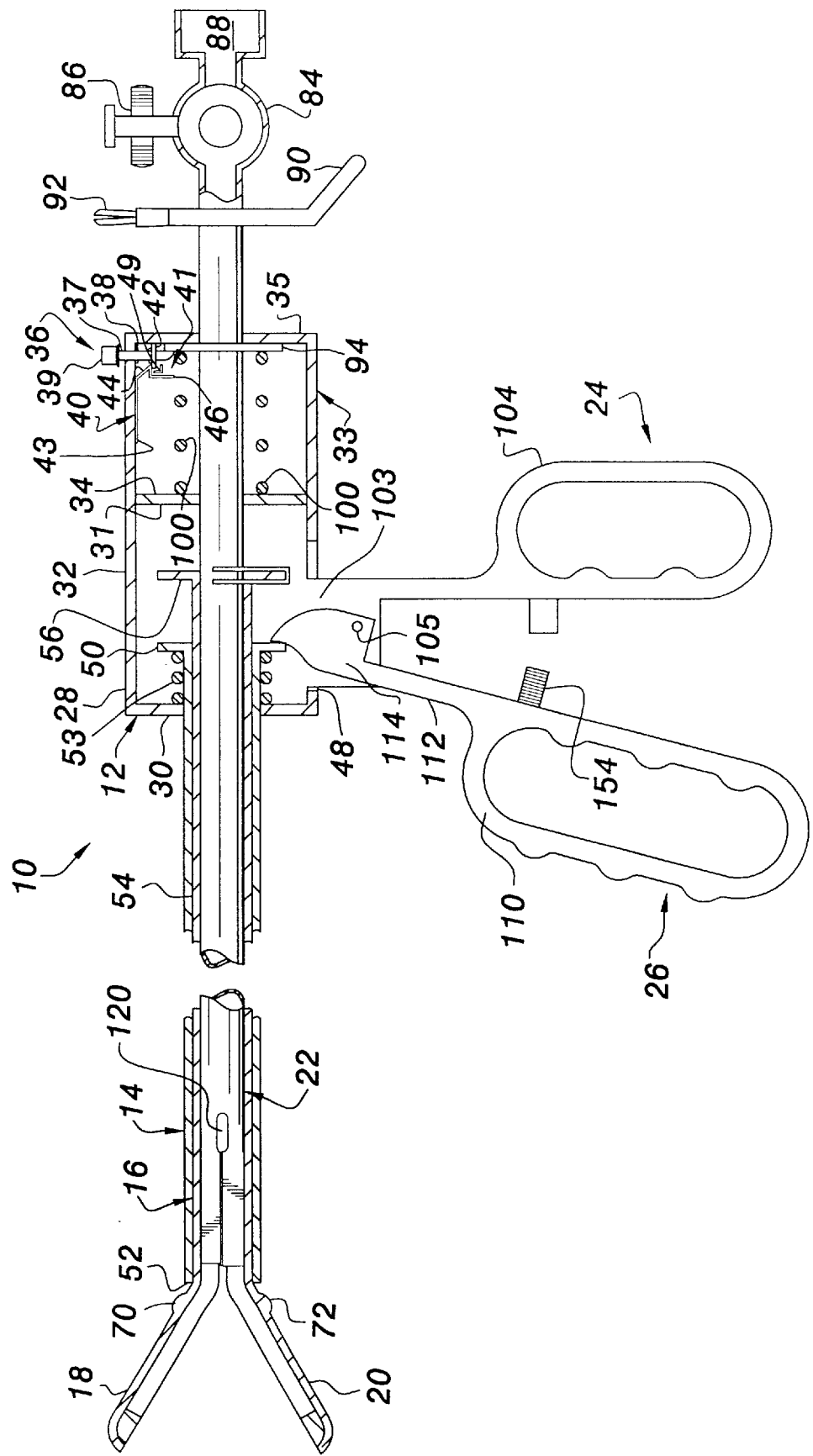
FIG. 12 is a sectional view of the preferred embodiment with the jaws open and the inner member retracted.

Endoscopic instrument 10 is advanced distally through portal sleeve 156 until jaws 18 and 20 emerge into the anatomical cavity. At this point, jaws 18 and 20 can be opened to permit visualization by an endoscope through tubular shaft 74 or can remain closed in the case of using a separately positioned endoscope. If jaws 18 and 20 are to be opened, this is accomplished by exerting finger pressure on finger loops 104 and 110 to release protrusion 152 and 154 to spread the loops apart as shown in FIG. 12 due to the force of biasing member 53. Pivotal movement of finger loop 110 about pin 105 permits flange 50 to move proximally with respect to intermediate member 16. This causes distal end 52 of outer member 14 to slide off cams 70 and 72 in a proximal direction allowing jaws 18 and 20 to spread apart elastically, as illustrated in FIG. 12.

Instrument 10 can be moved within the anatomical cavity with jaws 18 and 20 in either the open or closed condition depending on the type of visualization utilized and the desirability of presenting a narrow or wide jaw profile during movement. In FIG. 13, jaws 18 and 20 are shown in the opened condition for being positioned around anatomical tissue T to be grasped. Tissue T is located between tissue grasping inserts 62 and 64 so that when jaws 18 and 20 are partly closed, for example by placing finger pressure on the handles 24 and 26 to close jaws 18 and 20, tissue T will be held securely within the small gap between the jaws 18 and 20 as shown in FIG. 14.

Alternatively, for a biopsy specimen removal operation, inner member 22 can be advanced distally with jaw 18 and 20 either opened or closed, until biopsy box members 82 and 84 are positioned in slots 68, respectively. In this state, when jaws 18 and 20 are closed around tissue T, a biopsy specimen is cut from tissue T in the following manner. First, safety mechanism 36 is released by pressing down on push-button 39 to cause annular flange 42 formed on post 37 to engage trigger leg 51 rotating trigger 41 clockwise in FIG. 2. Trigger 41 is spring-biased in a counterclockwise direction and will thus return to its original position once annular flange 42 advances beyond trigger leg 51. When pressure on push-button 39 is released, safety bias member 38 will draw the post 37 upward in FIG. 2 so that flange 42 will engage trigger leg 51 from the other side causing the trigger 41 to rotate counterclockwise and trigger leg 49 to bear against arm extension 46. Arm extension 46, and thus latching surface 45, are moved away from the post permitting bias member 38 to move post 37 to its unlocked position shown in FIG. 16 where flange 42 abuts outer cylindrical wall 28.

Figure 16:
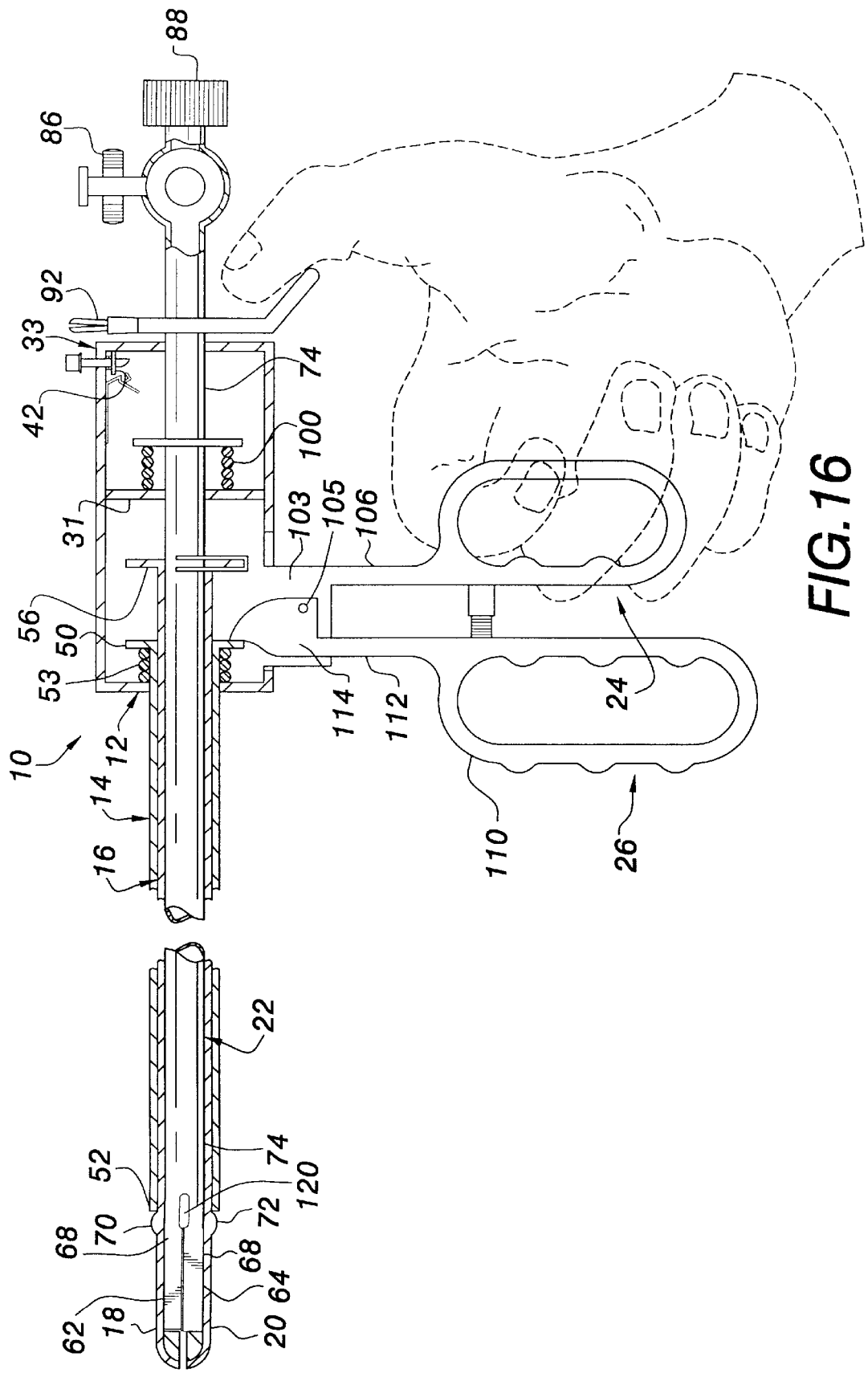
FIG. 16 illustrates the preferred embodiment is section with the jaws closed an the inner member advanced.

With safety 39 mechanism disabled, inner member 22 can be advanced by moving handle 90 toward housing 12. Biopsy box members 82 and 84 at the distal end of inner member 22 are aligned respectively with grooves 68 formed in jaw inserts 66, for example by use of splines formed along the length of inner member 22, and are slidable along grooves 68 to be positioned between jaws 18 and 20, as illustrated in FIGS. 15 and 16 when inner member 22 is advanced distally. The position of the surgeons hand, shown in phantom, in FIG. 16 is one example of how inner member 22 can be advanced. Since grooves 68 in this embodiment do not extend the entire length of jaws 18, the distal ends of grooves 68 can also serve as stops or abutments limiting the distal movement of biopsy box members 82 and 84 to protect surrounding organ structures and to allow a distal end of jaws 18 and 20 to be used for manipulation even when inner member 22 is advanced distally. Tissue T can be held between jaws 18 and 20 while a biopsy specimen is cut by biopsy box members 82 and 84 as biopsy box members 82 and 84 are pressed together until jaws 18 and 20 are opened, allowing further procedures, such as cauterization, to be performed with tissue T immobilized. As mentioned previously, tubular shaft 74 is hollow and can thus be utilized for creating suction during the procedure, performing aspiration or irrigation or to facilitate passage of additional instruments, such as an endoscope, or fluids into the anatomical cavity as desired through openings 120 and 121 defined in the biopsy tool (see FIG. 9). After a specimen is cut, inner member 22 can be retracted under the influence of bias ember 100 to pull biopsy box members 82 and 84 into intermediate member 16 or jaws 18 and 20 can be opened to release tissue T and instrument 10 can be withdrawn. Note that when inner member 22 is retracted in a proximal direction, as illustrated in FIG. 2, biopsy members 82 and 84 remain pressed together to preserve specimen S.

Figure 17:
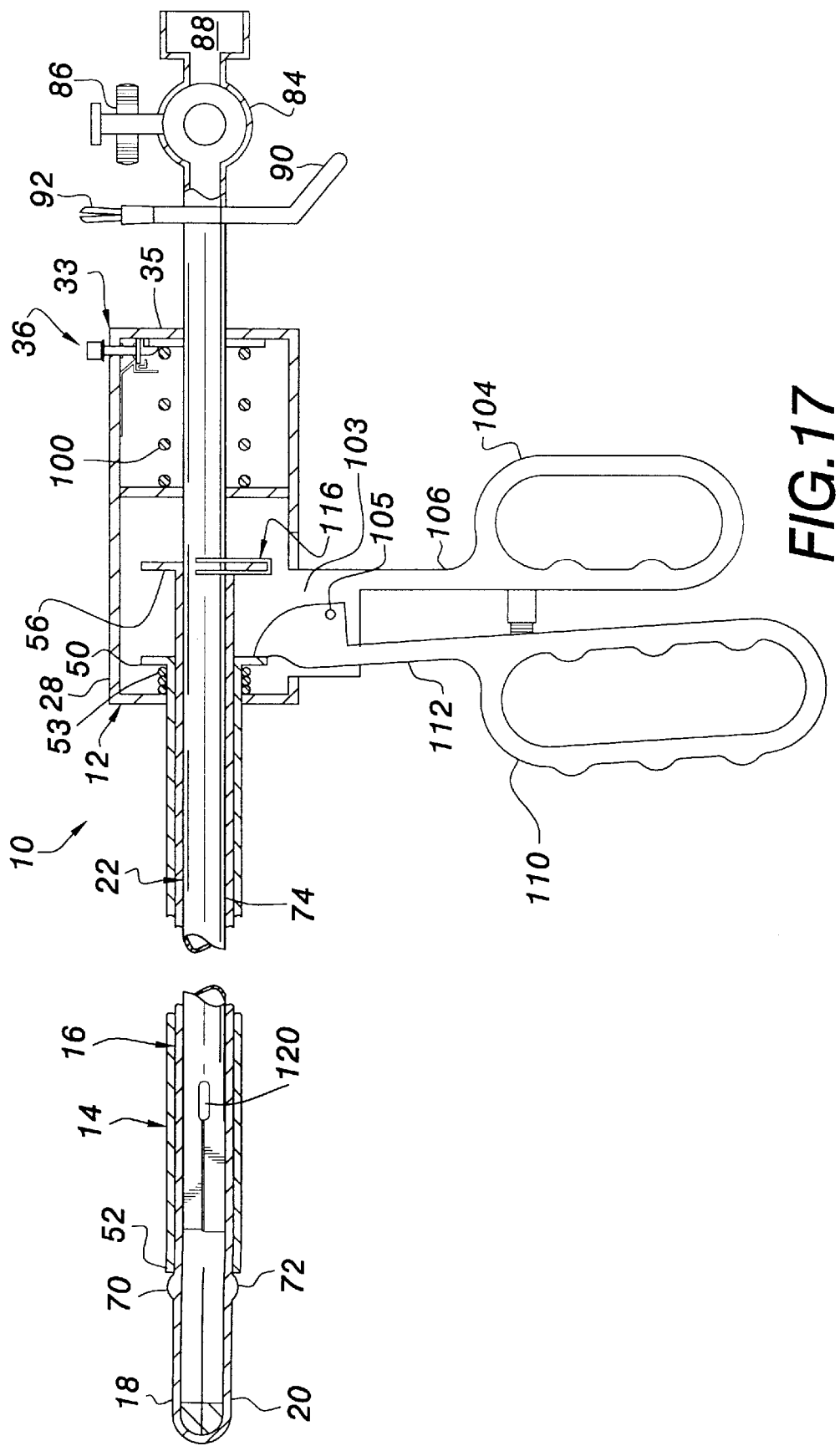
FIG. 17 illustrates the preferred embodiment is section with the jaws tightly closed an the inner member retracted.

As mentioned previously, tissue can be grasped and securely held or a biopsy specimen can be cut with jaws 18 and 20 in a partly closed state. However, for certain procedures it may be desirable to draw jaws 18 and 20 completely together as shown in FIG. 17, with or without objects held between the jaws. Jaws 18 and 20 can be closed completely or clamped together by drawing finger loops 104 and 110 towards one another until distal end 52 of outer member 14 slides farther distally over cams 70 and 72 to force jaws 18 and 20 into close contact with one another. If tissue or some other object is disposed between jaws 18 and 20, further advancement of outer member 14 over cams 70 and 72 will result in greater compression of the object. When loop handles 104 and 110 are drawn sufficiently close to one another, mating protrusions 152 and 154 will be engaged, locking handles 24 and 26 in their current position. If mating protrusions 152 and 154 are ratcheted as shown, various degrees of compression can be achieved and maintained without continuous finger pressure being applied.

FIG. 18 shows a modification of the jaws of endoscopic instrument 10 of the present invention in which jaws 18 and 20 include arcuate or concave portions 160 and 162, respectively, integrally-formed at opposed locations along the length of jaws 18 and 20. Arcuate portions 160 and 162 cooperate to define a substantially circular transverse passage through jaws 18 and 20 when closed and can thus hold a tubular organ, other anatomical tissue or an object therebetween for being manipulated or biopsied without compressing or flattening the organ, tissue or object. Tissue gripping surfaces 66 are formed on the flat portions of jaws 18 and 20 and can be formed along arcuate portions 160 and 162 as well. Grooves 68 are interrupted by arcuate portions 160 and 162 but extend longitudinally along flat portions of jaws 18 and 20 and are aligned to form a track for guiding biopsy boxes 82 and 84 across arcuate portions 160 and 162. Biopsy boxes 82 and 84 can be curved to conform to jaws 18 and 20 if desired.

In another modification of the jaws of endoscopic instrument 10 of the present invention, shown in FIG. 19, lower jaw 20 is fixed and extends distally from tubular body 54 along a longitudinal axis of tubular body 54. Upper jaw 18 has cam 70 and is movable from an open position normally extending at an angle relative to the longitudinal axis of tubular body 54 to a closed position where it mates with fixed lower jaw 20. Fixed lower jaw 20 can also carry cam 72. Jaws 18 and 20 include tissue gripping surfaces 66 and grooves 68 formed in the tissue gripping surfaces to serve as a guide for biopsy boxes 82 and 84.

Inner member 22 shown in FIG. 20 is for use with jaws 18 and 20 of FIG. 19. Lower biopsy box 84 is fixed to extend longitudinally from tubular shaft 74 and upper biopsy box 82 is resiliently movable. Upper biopsy box 82 is biased away from fixed lower biopsy box 84 and, when fitted within jaw 18 as shown in FIG. 21, is movable toward fixed biopsy box 84 by closing movable jaw 18 against fixed jaw 20.

FIG. 21 illustrates the distal end of a modified outer member. Slots 15 are formed in outer member 14 to receive jaws 70 and 72 and thus maintain proper alignment of jaws 18 and 20.

From the above, it will be appreciated that the endoscopic instrument of the present invention permits multiple functions to be performed endoscopically by use of a forceps unit having an intermediate tubular member with jaws configured for grasping or holding objects such as anatomical tissue or needles and an inner member telescopically fitted within the forceps unit tubular member and carrying a biopsy tool which can be selectively advanced into the jaws. The intermediate member and jaws are preferably formed as an integral one-piece construction and are movably disposed within an outer member to permit sliding movement of the outer member over the jaws to close the jaws. The outer member and intermediate tubular member can be mounted to a housing and coupled using any suitable handle mechanism and linkages for producing relative movement between the jaws and the outer tubular member. Because the jaws are carried at the end of a tubular body, the forceps unit can be positioned within an anatomical cavity and an inner member can be advanced distally through the tubular body. Because the inner member carries a biopsy tool, the biopsy tool can be selectively placed in the jaws. The inner member can also have a hollow tubular shaft open at a distal end for facilitating visualization with a conventional endoscope, illumination with fiber optics or other suitable light sources, for passage of implements such as blades or ligature appliers to cooperate with instruments mounted at the distal end of the inner member tubular shaft, and/or for introducing or collecting fluids prior to, during or after an operative step, is completed.

The jaws of the present invention can be straight, curved and/or angled and can have integrally formed or removable inserts with configurations for grasping and holding tissue and objects such as needles. Note that, while the jaws are discussed generally above as part of forceps, the jaws can be used to grasp a needle or other object for suturing or the like. The inserts can have any combination or number of longitudinal grooves formed in the inserts for accommodating biopsy tools. The grooves can extend part way along the inserts to define stops or abutments limiting distal movement of the biopsy tool or can extend the complete length of the inserts to form openings or apertures at a distal end of the jaws to allow passage of the biopsy tool to or beyond the distal end of the jaws. The jaws can have any shape in cross-section when closed, including circular, elliptical, rectangular and polygonal configurations, and can have opposed arcuate or concave portions for clamping tubular objects without compressing the objects.

Integral blades can be carried by one or both jaws and centrally located for cutting anatomical tissue or can be offset laterally from the central longitudinal axis of the jaws to permit better visualization and the formation of a longitudinal groove for passage of other operating members through the jaws. If a single blade is carried by one jaw, the other jaw can carry an opposed blade in a manner to permit sliding contact with scissor-like cutting, direct abutment of cutting edges to produce a chopping cut, and/or can form a pocket for receiving the cutting edge of the opposed blade to permit partial or complete closure of the jaws together.

The biopsy boxes can be formed integrally on the distal end of the inner member, as shown, or can be pivotally mounted by a pin or the like on the distal end. If pivotally mounted, a spring can be used to bias the boxes apart.

When the jaw inserts are removable, the empty cavities defined by the jaws can be used for accommodating cartridges holding surgical staples or clips such that by closing the jaws the staples or clips can be applied to anatomical tissue. Moreover, the elongate tubular structure of the inner member permits a series of cartridges to be carried therein for being applied individually within the anatomical cavity without removal of the inner member.

The position of the electrical connector opposite the handle is merely exemplary of the many various locations at which an electrical connector can be positioned. For example, an electrical connection could be made directly with the housing to utilize the jaws as conductive elements for performing electrosurgery. Also, inner surfaces of any of the tubular members can be electrically insulated to permit passage of electrosurgical instruments therethrough.

The handles and linkages shown and described herein for sliding the outer member over the jaws are exemplary of the types of conventional handle mechanisms suitable for performing the function of closing the jaws. However, the handles can have any configuration for producing relative movement between the outer and intermediate members, including two pivoted legs with finger loops and sliding brackets as disclosed in the parent application, one fixed and one pivoted leg with finger loops, a pistol grip with a movable trigger, or resilient U-shaped members connected between outer and intermediate members. Moreover, the handles can have any orientation relative to the longitudinal axis of the instrument including, for example, substantially transverse orientations whereby the handles extend transversely from a sidewall of the housing or substantially longitudinal orientations whereby the handles extend longitudinally from a rear wall of the housing and are operated like a scissors or even rotatable configurations whereby the handles can be moved between transverse and longitudinal orientations as desired by selectively disengaging the handles from the jaws. Suitable linkages include brackets with sliding motion, gears and/or racks mounted on or between handles and the outer and intermediate members, pulleys and cords or any other direct or indirect coupling mechanisms.

The intermediate and outer members can be frictionally fitted to maintain a position by resisting relative movement, can be biased apart with a bias member such as a torsion spring connected between the handles or a helical coil spring disposed around the intermediate member and held in compression between intermediate and outer member flanges, or can be biased together as desired. If the outer tubular member is biased relative to the intermediate member, a mechanism can be provided for locking/releasing the bias member to permit the outer tubular member to be maintained at any position relative to the jaws, for example by frictional engagement.

The components of the endoscopic instrument of the present invention can be made of any suitable, medical grade materials to permit sterilization for re-use or for single patient use. The components can be made of multiple parts of various configurations and materials to reduce cost. The instrument can have various valves, stop cocks and seals to control fluid flow therethrough, such as valve 58 schematically shown in phantom in FIG. 2.

The features of the various embodiments described above can be combined in any manner desired dependent upon the operational requirements of the procedure to be performed and the complexity of the endoscopic instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A surgical instrument comprising
   a tubular outer member having a proximal end and terminating distally at a distal end;
   an intermediate member having a tubular body disposed telescopically within said outer member and a distal end defining a pair of opposed jaws resiliently biased apart;
   an inner member comprising a shaft and a biopsy tool at a distal end of said shaft, said inner member being slidably disposed at least partly within said intermediate member;
   a handle coupled with at least one of said intermediate member and said outer member and configured to create relative movement between said intermediate member and said outer member, whereby said pair of opposed jaws is moved between open and closed positions when said distal end of said outer member is moved relative to said jaws.

2. An instrument as recited in claim 1 wherein said jaws define opposed grasping surfaces.

3. An instrument as recited in claim 2 wherein a longitudinal groove is formed in one of said grasping surfaces.

4. An instrument as recited in claim 3 wherein said longitudinal groove extends part way along said one of said grasping surfaces to define a stop limiting distal movement of said biopsy tool advanced along said groove.

5. An instrument as recited in claim 3 wherein said longitudinal groove extends along an entire length of said one of said grasping surfaces to define an aperture at a distal end of one of said jaws.

6. An instrument as recited in claim 2 wherein a longitudinal groove is formed in each of said grasping surfaces.

7. An instrument as recited in claim 6 wherein said longitudinal grooves extend part way along said grasping surfaces to define a pair of stops limiting distal movement of said biopsy tool advanced along said grooves.

8. An instrument as recited in claim 6 wherein said longitudinal grooves extend along entire lengths of said grasping surfaces to define an aperture at a distal end of said jaws.

9. An instrument as recited in claim 6 wherein said biopsy tool comprises a pair of opposed biopsy boxes that can be advanced respectively along said grooves.

10. An instrument as recited in claim 1 wherein said jaws include opposed arcuate portions defining an opening between said jaws.

11. An instrument as recited in claim 1 wherein one of said jaws is fixed parallel to a longitudinal axis of said intermediate member and the other of said jaws is movable.

12. An instrument as recited in claim 11 wherein said biopsy tool comprises a pair of opposed biopsy boxes, one of said biopsy boxes being fixed parallel to the longitudinal axis and the other of said biopsy boxes being movable.

13. An instrument as recited in claim 9 wherein said biopsy boxes are biased apart to fit within said grooves when advanced between said jaws.

14. A method of performing surgical procedures comprising the steps of introducing a tubular member with jaws formed in an end thereof through an opening in an anatomical cavity wall;
   grasping anatomical tissue with said jaws;
   releasing the anatomical tissue;
   advancing an inner member having a biopsy tool distally through said tubular member; and
   performing a medical procedure with said inner member.

15. A method as recited in claim 14 wherein said performing step includes the step of using said inner member to perform at least one of the functions of cauterizing, collecting a biopsy, creating suction, irrigating and aspirating.

16. A method as recited in claim 14 wherein said introducing step includes closing said jaws by sliding a tubular outer member over said jaws.

17. A method as recited in claim 16 wherein said grasping step includes sliding said outer member proximally with respect to said jaws to permit said jaws to resiliently separate, positioning the anatomical tissue between said jaws and sliding said outer member distally with respect to said jaws to close said jaws around the anatomical tissue.

18. A method of performing surgical procedures comprising the steps of introducing a tubular member with jaws through an opening in an anatomical cavity wall;

advancing an inner member carrying a biopsy tool distally through said tubular member until said biopsy tool is positioned between said jaws; and performing a medical procedure with said inner member.

19. A method as recited in claim 18 wherein said performing step includes using said inner member to perform at least one of the functions of cauterizing, collecting a biopsy, creating suction, irrigating and aspirating.

20. A surgical instrument comprising a tubular outer member having a proximal end and terminating distally at a distal end, a channel being defined through said outer member;

an intermediate member having a body disposed at least partly within said outer member and a distal end defining a pair of opposed jaws resiliently biased apart;

an inner member comprising a shaft and a biopsy tool at a distal end of said shaft, said inner member being slidably disposed at least partly within said channel;

a handle coupled with at least one of said intermediate member and said outer member and configured to move said pair of opposed jaws between open and closed positions.

21. An instrument as recited in claim 20 wherein said channel passes through said intermediate member.

* * * * *